United States Patent
Doric et al.

(10) Patent No.: US 9,846,300 B2
(45) Date of Patent: Dec. 19, 2017

(54) MICROSCOPE WITH MULTIPLE IMAGE SENSORS FOR FLUORESCENCE IMAGING OF MULTIPLE LOCATIONS AND/OR WAVELENGTHS

(71) Applicant: Optomak, Inc., Quebec (CA)

(72) Inventors: Sead Doric, L'Ancienne-Lorette (CA); Harold Dehez, Quebec, Quebec (CA)

(73) Assignee: OPTOMAK, INC. (CA)

( * ) Notice: Subject to any disclaimer, the term of this patent is extended or adjusted under 35 U.S.C. 154(b) by 11 days.

(21) Appl. No.: 15/232,371

(22) Filed: Aug. 9, 2016

(65) Prior Publication Data

US 2017/0199369 A1    Jul. 13, 2017

Related U.S. Application Data

(63) Continuation-in-part of application No. 14/991,208, filed on Jan. 8, 2016.

(51) Int. Cl.
*G02B 21/36* (2006.01)
*G02B 21/00* (2006.01)
(Continued)

(52) U.S. Cl.
CPC .......... *G02B 21/361* (2013.01); *A61B 5/0071* (2013.01); *G02B 21/0008* (2013.01);
(Continued)

(58) Field of Classification Search
CPC .. G02B 21/36; G02B 21/361; G02B 21/0008; G02B 21/06; G02B 21/16; G02B 21/18;
(Continued)

(56) References Cited

U.S. PATENT DOCUMENTS 5,034,010 A * 7/1991 Kittrell .............. A61B 1/00096
600/478
5,318,024 A * 6/1994 Kittrell .............. A61B 1/00096
600/478
(Continued)

FOREIGN PATENT DOCUMENTS

WO    WO 2016187715 A1    12/2016
WO    WO 2017079688 A1    5/2017

OTHER PUBLICATIONS

U.S. Appl. No. 62/383,122, filed Sep. 2, 2016, 132 pages (pp. 1-132 in pdf).
(Continued)

*Primary Examiner* — William R Alexander
(74) *Attorney, Agent, or Firm* — Mitch Harris, Atty at Law, LLC; Andrew M. Harris

(57) ABSTRACT

A miniaturized microscope provides the combined capability for simultaneous or sequential fluorescence imaging at two different wavelengths and/or at two different object planes within a sample to which a cannula is attached. The microscope includes an illumination input connector for connecting one or more illumination sources, a connector for connecting the microscope to the cannula, a pair of optical image sensors for imaging the two different object planes and/or wavelengths and a pair of optical splitters: one for separating the illumination from light returning from the sample and the other for splitting the light returning from the sample into two images and providing the two images to their corresponding image sensor.

23 Claims, 9 Drawing Sheets

(51) Int. Cl.
*G02B 21/16* (2006.01)
*G02B 21/06* (2006.01)
*G02B 21/18* (2006.01)
*G02B 27/14* (2006.01)
*A61B 5/00* (2006.01)

(52) U.S. Cl.
CPC ............. *G02B 21/06* (2013.01); *G02B 21/16* (2013.01); *G02B 21/18* (2013.01); *G02B 21/36* (2013.01); *G02B 27/141* (2013.01)

(58) Field of Classification Search
CPC .... G02B 27/141; A61B 5/0071; A61B 5/0059
USPC ....................................................... 359/363
See application file for complete search history.

(56) References Cited

U.S. PATENT DOCUMENTS

| | | | |
|---|---|---|---|
| 6,101,028 A | 8/2000 | Heacock et al. | |
| 6,508,759 B1 | 1/2003 | Taylor et al. | |
| 6,643,071 B2 | 11/2003 | Schnitzer | |
| 6,846,311 B2 | 1/2005 | Gatto | |
| 6,847,480 B2 | 1/2005 | Steenblik et al. | |
| 7,262,923 B2 | 8/2007 | Quake et al. | |
| 7,761,139 B2* | 7/2010 | Tearney | A61B 5/0066 600/473 |
| 8,346,346 B1 | 1/2013 | Schnitzer et al. | |
| 8,624,967 B2 | 1/2014 | O'Connell et al. | |
| 8,840,566 B2 | 9/2014 | Seibel et al. | |
| 9,046,659 B2 | 6/2015 | Doric | |
| 9,195,043 B2 | 11/2015 | Ghosh et al. | |
| 9,207,405 B2 | 12/2015 | Doric | |
| 9,409,036 B2 | 8/2016 | Klorg | |
| 9,476,832 B2 | 10/2016 | Walla et al. | |
| 9,696,897 B2 | 7/2017 | Garcia | |
| 2002/0045811 A1* | 4/2002 | Kittrell | A61B 1/00096 600/407 |
| 2005/0004453 A1* | 1/2005 | Tearney | A61B 5/0066 600/427 |
| 2008/0151263 A1* | 6/2008 | Randers-Pehrson | C40B 60/12 356/601 |
| 2010/0007947 A1 | 1/2010 | Lembke | |
| 2011/0224554 A1 | 9/2011 | Vukeljic | |
| 2014/0036364 A1 | 2/2014 | Doric | |
| 2015/0309295 A1 | 10/2015 | Cocker et al. | |
| 2015/0366437 A1 | 12/2015 | Labrie et al. | |
| 2016/0131334 A1 | 5/2016 | Rousseau et al. | |
| 2017/0059841 A1 | 3/2017 | Trulson et al. | |
| 2017/0199364 A1* | 7/2017 | Doric | G02B 21/082 |

OTHER PUBLICATIONS

U.S. Appl. No. 62/251,501, filed Nov. 5, 2015, 70 pages (pp. 1-70 in pdf).

Notice of Allowance in U.S. Appl. No. 14/991,208 dated Jul. 26, 2017, 10 pages (pp. 1-10 in pdf).

Notice of Allowance in U.S. Appl. No. 14/991,208, dated Jun. 2, 2017, 9 pages (pp. 1-9 in pdf).

Ghosh, et al., "Miniaturized integration of a fluorescence microscope", Nature Methods, Oct. 2011, pp. 871-882, vol. 8, No. 10, Nature Publishing Group, London.

Ziv, et al., "Long-term dynamics of CA1 hippocampal place codes", Nature Neuroscience, Feb. 2013, 5 pages (pp. 1-5 in pdf), 16(3).

Flusberg, et al., "High-speed, miniaturized fluorescence microscopy in freely moving mice", Nature Methods, Nov. 2008, pp. 935-938, vol. 5, No. 11, Nature Publishing Group, London.

Office Action in U.S. Appl. No. 14/991,208 dated May 4, 2017, 10 pages (pp. 1-10 in pdf).

Helmchen, et al., "A Miniature Head-Mounted Two-Photon Microscope: High-Resolution Brain Imaging in Freely Moving Animals", Neuron, Sep. 27, 2001, pp. 903-912, vol. 31, Cell Press.

Murakami, et al., "A Miniature Confocal Optical Microscope with MEMS Gimbal Scanner", 12$^{th}$ International Conference on Solid-State Sensors, Actuators and Microsystems, Jun. 8-12, 2003, pp. 587-590, Boston, US.

Bergeron, "Fingertip-size microscope has huge potential for studying the brain and its diseases, say Stanford researchers", Sep. 16, 2011, downloaded from http://news.stanford.edu/news/2011/september/fingertip-size-microscope-091611.html on Apr. 30, 2017, 6 pages (pp. 1-6 in pdf).

Baker, "Abbas El Gamal and Mark Schnitzer: Two-gram microscopes make brain images in moving mice", Nature Methods, Oct. 2011, pp. 781, vol. 8, No. 10, Nature America, Inc.

* cited by examiner

US 9,846,300 B2

MICROSCOPE WITH MULTIPLE IMAGE SENSORS FOR FLUORESCENCE IMAGING OF MULTIPLE LOCATIONS AND/OR WAVELENGTHS

This U.S. patent application is a Continuation-in-Part of U.S. patent application Ser. No. 14/991,208, filed on Jan. 8, 2016, and claims priority thereto under 35 U.S.C. §120. The disclosure of the above-referenced U.S. patent application is incorporated herein by reference.

BACKGROUND OF THE INVENTION

1. Field of the Invention

The present invention relates to biological microscopy, and more particularly concerns a microscope probe for in vivo or in vitro fluorescence imaging of multiple locations and/or wavelengths using multiple image sensors integrated within the microscope.

2. Background of the Invention

When making microscopic observations of in vivo biological specimens, minimally invasive techniques are required. However, conventional microscopes feature large size microscope objectives. Large objectives cannot be implanted within a sample without causing significant damage to the sample, such as removing structures in order to facilitate access to deep layers within the sample. Less invasive fiber-optic cannulae that are typically used in optogenetics experiments are typically configured only for optical stimulation or silencing of a certain class of neurons without imaging capabilities. More recent solutions include miniaturized microscopes that can be detachably coupled to a base plate mounted on a subject, such as those disclosed in U.S. Pat. No. 9,195,043 and U.S. Patent Application Publication U.S. 20150309295.

While miniaturized microscopes are available, as noted above they are limited in their flexibility of performing fluorescence measurements.

Therefore, it would be desirable to provide an optogenetic compatible fluorescence microscope with additional facilities.

SUMMARY OF THE INVENTION

The invention encompasses microscopes capable of performing fluorescence imaging on a sample having an attached optical cannula, which is a fixture on the sample having one or more optical probes focusing and/or extending into the sample for delivering light into and receiving light from regions or points within the sample. The invention also encompasses a method of performing fluorescence imaging on a sample.

The microscope includes a first connector for receiving an optical illumination connection coupling light from one or more illumination sources and a second connector adapted to mechanically connect to the cannula. The second connector includes an optical interface for coupling light returning from the sample to the microscope and coupling illumination from the illumination sources to the sample. The microscope further includes a pair of optical splitters: a first optical splitter that separates the light returning from the sample from the illumination light provided to the second connector, and a second optical splitter for splitting the light returning from the sample into two images, which are provided to corresponding image sensors within the microscope.

The second optical splitter may be an optical filter that splits light of two different wavelengths returning from the sample, or may be an intensity-division or polarization beam-splitter in the case in which the two different images are of the same wavelengths, but from two different object planes, e.g., depths within the sample.

The foregoing and other objectives, features, and advantages of the invention will be apparent from the following, more particular, description of the preferred embodiment of the invention, as illustrated in the accompanying drawings.

BRIEF DESCRIPTION OF THE DRAWINGS

The novel features believed characteristic of the invention are set forth in the appended claims. The invention itself, however, as well as a preferred mode of use, further objectives, and advantages thereof, will best be understood by reference to the following detailed description of an illustrative embodiment when read in conjunction with the accompanying drawings, wherein like reference numerals indicate like components, and:

DESCRIPTION OF ILLUSTRATED EMBODIMENT

Figure 1:
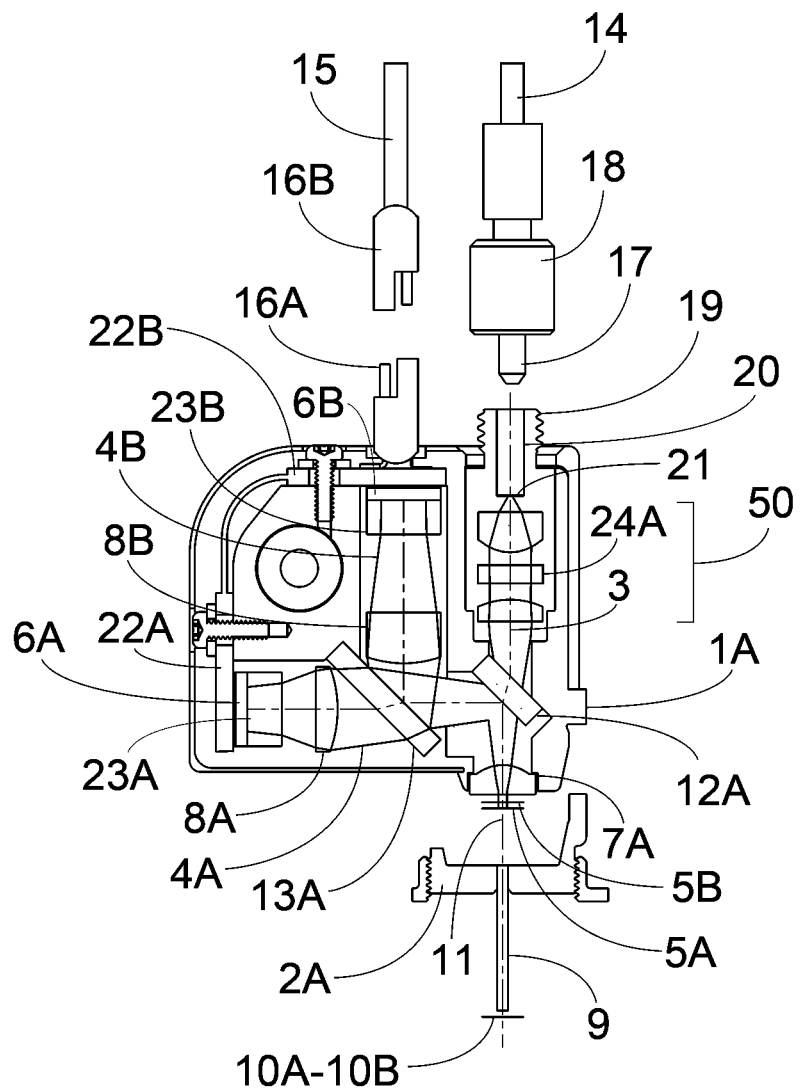
FIG. 1 is a side cross-section view of an exemplary miniaturized microscope system.

The systems described herein are miniaturized multi-imaging systems of generally less than a cubic inch in size that combine capability for imaging of two different images, which may be two different colors (wavelengths) or imaging two different object planes using a pair of internal image sensors. Typical multi-color microscopes are bulky and traditionally limited to tabletop applications. An application for the microscopes disclosed herein is fluorescence imaging of fluorescent proteins for applications requiring monitoring of cell activity. The system includes an objective lens to create a magnified image of one or two regions of the sample on two (or more) image sensors integrated within the microscope. The objective lens may be integrated in the microscope or be integrated in a cannula to which the microscope is attached. The microscope includes two optical splitters: one to separate illumination light from fluorescence signals and another to separate the fluorescence signals into two images for measurement by the image sensors.

In some applications, a sample may be labeled with two different fluorescent markers having distinct fluorescence emission spectra and distinct excitation spectra, which avoids cross-talk between measurement channels. While the first marker is used to measure activity, the second marker may be present as a reference, or also for cell activity monitoring. Providing two different fluorescence measurement channels provides for simultaneous capture of images due to the presence of the two fluorescent markers. In other applications, the two channels can be configured to image two different object planes at different depths within the sample. The microscope also includes a connection for receiving illumination light from one or more external light sources with an optical arrangement to bring illumination light to the subject for fluorescence imaging. For multi-color measurement, light from two illumination sources can be combined and provided to the illumination connection, or for sequential multi-color measurement, two different illumination sources can be sequentially connected. For measurements of the same wavelength at different object planes, only one illumination source may be required.

The miniaturized microscope disclosed herein is configured to easily connect to and disconnect from the cannula and includes a specific connector adapted to provide precise optical alignment with the cannula, which may be a cannula such as those described in U.S. Patent Application Publication US20150366437A1, the disclosure of which is incorporated herein by reference and also in the above-incorporated parent U.S. patent application. The imaging system is designed to observe one or many fields of view smaller than 0.5 mm$^2$ (to reduce invasiveness) with a spatial resolution at the micron scale. An optical splitter set is included to separate one or more bands of illumination light from the fluorescence signal returning from the sample, to provide the illumination light to the sample, and to separate the fluorescence signals and direct them to corresponding image sensors. The objective lens may be incorporated in the microscope body, or in the cannula and may image light from an implant inserted in the sample, which may be a relay lens, e.g. a GRIN lens, and/or a glass rod. Alternatively, the objective lens may image one or more regions near the surface of the sample or at some depth within a transparent or translucent sample. Other configurations and combinations, such as those disclosed herein or otherwise provided by combining elements that are shown by the present disclosure or their equivalents, are contemplated and the examples chosen as illustrations should not be considered limiting. In the examples given herein, the field of view of the microscope described herein is less than 0.5 mm$^2$ and having a spatial resolution at the micron scale, which also differs from existing miniature microscope systems. By limiting the field of view to less than 0.5 mm$^2$, the volume of the microscope can be reduced and the image quality improved over the field of view. To improve the portability and facilitate the access to a confined region of interest, the total size of the miniaturized microscope can be maintained below 1 in$^3$ with a weight of under 4 g.

Referring now to FIG. 1, an example of a miniaturized microscope system for fluorescence measurement is shown in a side cross-section view, respectively. A microscope body 1A has a connector adapted for connection to a cannula 2A that is attached to a sample, which is generally a biological test specimen for in vivo measurements as described in the above-incorporated U.S. patent applications. The microscope, which includes microscope body 1A, also includes an optical interface at two different object planes 5A and 5B of the optical system below an objective lens 7A. In the illustrated microscope, two object planes 10A and 10B are co-located, i.e., they are at the same depth within a sample to which cannula 2A is attached. Due to optical path length differences due to a difference in wavelength for the two images generated by the microscope system of FIG. 1, co-located object planes 10A and 10B of the system are imaged on object planes 5A and 5B, respectively, of microscope body 1A. Object planes 5A and 5B are not co-located, and the corresponding detection pathways 4A and 4B to a pair of corresponding image sensors 6A and 6B differ. Image sensors 6A and 6B may be CMOS or CCD sensors mounted to corresponding circuit boards 22A and 22B, and are interfaced to an external image processing system via an electrical cable 15 terminated at a high speed connector 16B and connected to microscope body 1A via another high speed connector 16A that provides an interface to signals on printed circuit boards 22A and 22B.

Figure 7:
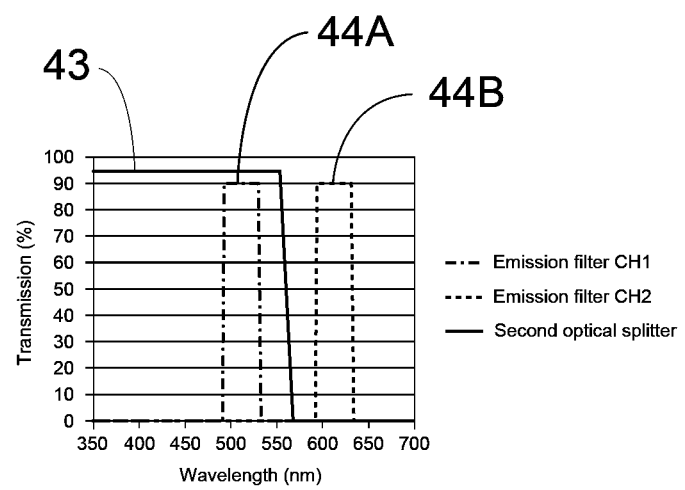

A first optical splitter 12A, which in the illustrated embodiment is a dichroic filter, directs light returning from the sample that contains both images corresponding to two different wavelengths of fluorescent emissions from the location of object planes 10A and 10B toward a second optical splitter 13A. First optical splitter 12A is generally a dual-bandpass filter designed to pass illumination of two different excitation wavelengths, and thus has pass-bands centered around the excitation wavelengths and reflects both of the fluorescence wavelengths to direct the light returning from the sample to second optical splitter 13A. In some applications, the excitation wavelength is a single excitation wavelength that excites two spectrally distinct fluorescence markers, e.g., Förster resonance energy transfer (FRET) applications. In such applications, first optical splitter 12A will generally have a short-pass filter dichroic characteristic. Second optical splitter 13A, in the depicted embodiment, is also a dichroic filter that divides the light returning from the sample into two images, one provided at image sensor 6A via transmission through optical splitter 13A and the other provided at image sensor 6B by reflection from optical splitter 13A, which is inclined at 45 degrees. A pair of corresponding emission filters 23A and 23B, which are generally single-passband filters, are provided to remove stray light, illumination leakage and leakage from the other channel from the fluorescence signals corresponding to the images of object planes 10A and 10B provided to image sensors 6A and 6B, respectively. Therefore, emission filters 23A and 23B have pass-bands 44A and 44B, as shown in FIG. 7, centered on the respective wavelengths of the corresponding fluorescent markers that are measured by respective image sensors 6A and 6B.

A pair of lenses 8A and 8B provide adjustment of the magnification between object planes 5A-5B and image sensors 6A-6B. To optimize aberration correction and increase the numerical aperture of the objectives, a high numerical aperture lens is used as objective lens 7A. In the illustrated embodiment, the numerical aperture of objective lens 7A is between 0.3 and 0.5. To reduce the total size of the system, the focal length of the objective lens, the length of the detection pathways 4A-4B, and the focal length of lenses 8A-8B are chosen to produce a magnification ratio between 2× and 10× between object planes 5A-5B and image sensors 6A-6B. The lengths of the detection pathways 4A-4B and the focal length of the lenses 8A-8B are adjusted to obtain the same magnification in both detection pathways 4A-4B. The insertion of lenses 8A-8B in detection pathways 4A-4B also reduces the angular divergence at the surface of emission filters 23A-23B and therefore improves the efficiency of emission filters 23A-23B. In the depicted embodiment, a lens 9 may also be used to relay the images of object planes 10A-10B within the subject to the respective object planes 5A-5B of the microscope body.

In the depicted example, lens 9, which in the depicted embodiment is a gradient index (GRIN) relay lens, extends into the sample to image a region of interest within the sample at two different wavelengths providing images of object planes 10A and 10B at different wavelengths and the same depth. GRIN relay lens 9 is integrated in cannula 2A and is optically aligned with the optical axis 11 of the objective lens 7A. GRIN relay lens 9 is not required for imaging surfaces just below cannula 2A. In other embodiments illustrated below, the objective lens is integrated in a cannula and no relay lens is used. An illumination pathway 3 extends from a connector 19 at the top of microscope body 1A that receives an optical coupling, such as an optical fiber, from one or more illumination sources that provide light of at least one nominal wavelength for exciting fluorescence in the sample. The depicted microscope system further includes an optical patch cord 14, e.g., multi-mode optical fiber or fiber bundle that conducts the illumination light from the external illumination source. A threaded female connector 18 mates with male threaded connector 19 of microscope body 1A to secure optical patch cord 14 to microscope body 1A. Connector 18 may be of a standard type for connection to various illumination sources, which may include laser diodes, solid state lasers, gas lasers, fiber lasers, etc. In the particular embodiments described herein, the illumination source is a laser, LED or Ce:YAG incoherent illumination source providing illumination for imaging of cells in biomedical applications. A bored recess 20 in microscope body 1A receives a ferrule 17 that holds the terminated end of optical patch cord 14, which contacts a hub 21 providing an optical interface receiving the illumination light, i.e., the light for fluorescence excitation, which is directed to an optical interface at object planes 5A-5B of objective lens 7A for introduction to GRIN relay lens 9 in cannula 2A. An illumination lens system 50 forms a collimated beam along illumination pathway 3 that is filtered by an excitation filter 24A, and which is then collimated at the object plane(s) of the objective lens 7A, for introduction to GRIN relay lens 9 in cannula 2A along optical axis 11 after passing through optical splitter 12A. Excitation filter 24A includes at least one optical transmission band corresponding to the nominal wavelength of the illumination source coupled through connector 19 and cleans the illumination light spectrum before it is introduced to GRIN relay lens 9, removing light artifacts such as auto-fluorescence generation in the optical fibers coupling the illumination light to connector 19.

Figure 2:
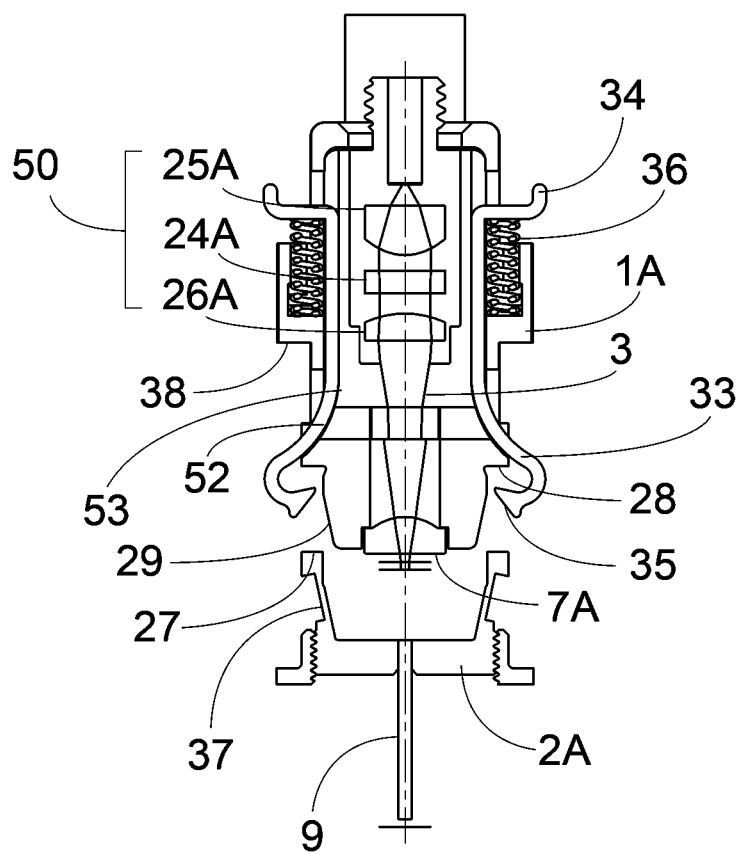
FIG. 2 is a front cross-section view of the exemplary miniaturized microscope system of FIG. 1.

Referring additionally now to FIG. 2, further details of the microscope shown in FIG. 1 are illustrated. Illumination lens system 50 includes a high numerical aperture aspheric lens 25A and a plano-convex spherical lens 26A, and forms a collimated beam that is filtered by excitation filter 24A. Illumination lens system 50 is configured to provide a collimated and uniform illumination over the entire field of view in object planes 5A-5B, in order to avoid artifacts due to illumination discontinuities. Illumination lens system 50 is configured so that the output of the optical fiber at the tip of ferrule 17 is imaged at the back focal plane of objective lens 7A, which ensures that defects or dust present at the interface of ferrule 17 after multiple connections and disconnections have been made are not imaged in object planes 5A-5B. A separate high numerical aperture aspheric lens 25A and plano-convex spherical lens 26A are not required. In alternative embodiments, a single high numerical aperture aspheric lens 25A may be used to focus illumination light at the back aperture of objective lens 7A. However, using two lenses reduces the angle of incidence of light at the surface of excitation filter 24A and thereby improves filtering efficiency.

Figure 3:
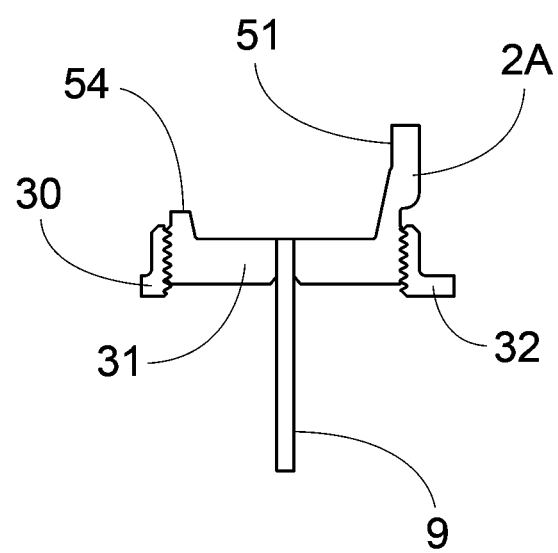
FIG. 3 is a side cross-section view of an exemplary cannula that can be used with the exemplary miniaturized multimodal microscope systems disclosed herein.

FIG. 2 and additionally FIG. 3 show further details of an attachment mechanism for cannula 2A, a cannula similar to which is described in detail in the above-incorporated Parent U.S. patent application U.S. Ser. No. 14/991,208. In the depicted embodiment, use of such a cannula provides convenient attachment and removal of microscope body 1A from cannula 2A, but is not a requirement to practice the invention, except as recited in particular Claims. Cannula 2A includes an orientation key 54 that provides rotational alignment of cannula 2A with microscope body 1A. An interior top surface 51 of cannula 2A is shaped to adapt cannula 2A to accept a guiding taper 29 around the bottom portion of microscope body 1A and a cylindrical shoulder 27 contacts a corresponding shoulder 28 on microscope body 1A to prevent movement of microscope body 1A with respect to cannula 2A once microscope body 1A is secured to cannula 2A. Shoulder 27 defines a slot 37 around the exterior surface of cannula 2A. A precise optical alignment between objective lens 7A and GRIN relay lens 9 is achieved once microscope body 1A is secured to cannula 2A. As seen in FIG. 2, additional components that secure microscope body 1A to cannula 2A are shown. Latch hooks 35 at the end of a pair of latches 33 capture shoulder 27 when latches 33 are expanded as inner surfaces of extensions 52 of latches 33 slide along side walls 53 of microscope body 1A. Side walls 53 of microscope body 1A are shaped to form an acute angle with respect to the cylindrical axis of the cannula 2A, so that, when latches 33 are moved downwards toward cannula 2A, side walls 53 act as guides for expanding latch hooks 35 to release shoulder 27 of cannula 2A. The upper end of latches 33 forms a retention shoulder 34 which compresses a compression spring 36 that provides for secure latching of latch hooks 35 by pressing against the lower surface of retention shoulder 34 and a shoulder 38 of microscope body 1A to pull latches 33 upwards. Cannula 2A and microscope body 1A are connected by pressing springs 36 and pressing on latches 33 toward cannula 2A. A pin may be inserted between latch hooks 35 and cannula 2A to release latch hooks 35 from slot 37. Cannula 2A is secured to the specimen being observed, in general, by fastening a flange 32 of cannula 2A to the specimen with an adhesive and/or with fasteners such as screws. The flange 32 is attached to a body 31 of cannula 2A. To adjust the focus and the working distance of the microscope system (or to adjust the penetration depth of GRIN relay lens 9 if present), cannula 2A includes an adjustment ring 30 that is glued and/or screwed on the specimen via flange 32. In the example, body 31 of the cannula 2A includes a male threaded portion on an outer surface. A threaded female inner surface of adjustment ring 30 mates with a threaded male portion of body 31 and is rotated to adjust the distance between the microscope system and the specimen (or the penetration depth of GRIN relay lens 9) when adjustment ring 30 is attached to the specimen.

Figure 4:
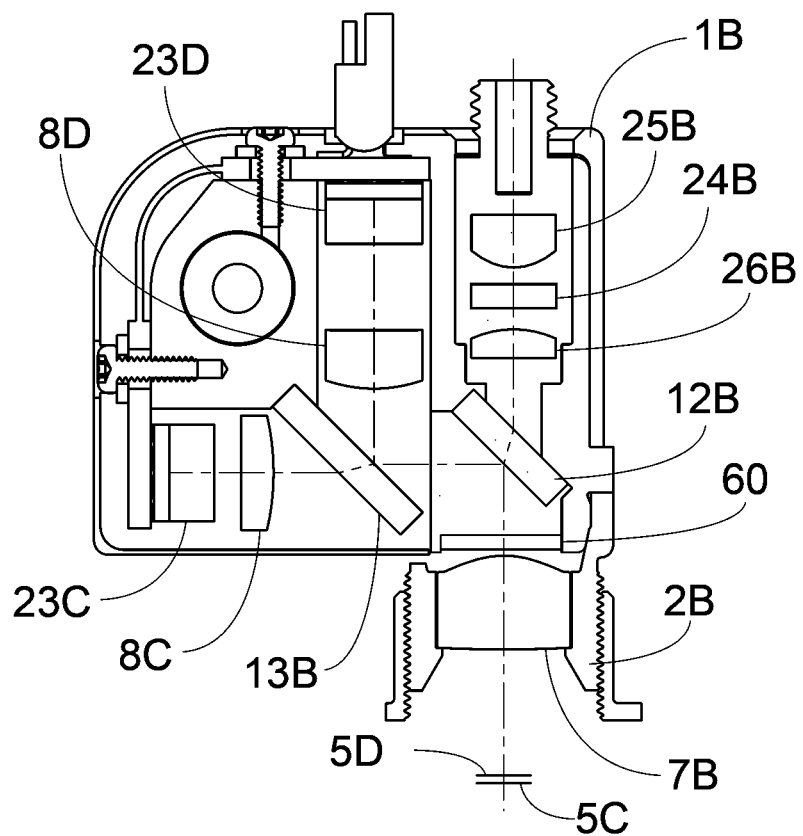
FIG. 4 is a side cross-section view of another exemplary miniaturized microscope system.

Referring now to FIG. 4, another example of a microscope system for fluorescence measurement is shown in a side cross-section view. The microscope system of FIG. 4 differs from the microscope system of FIGS. 1-2 in that an objective lens 7B is integrated in a cannula 2B detachably coupled to a microscope body 1B and is provided by a high numerical aperture type of objective lens 7B. Since the optical path differs from the microscope system of FIGS. 1-2, a high numerical aperture aspheric lens 25B, a plano-convex spherical lens 26B, an excitation filter 24B, optical splitters 12B and 13B, lenses 8C-8D, emission filters 23C-23D may be of different dimensions. Locating objective lens 7B in cannula 2B increases the working distance and image field of view up to 0.5 mm² without increasing invasiveness in the subject. There is no GRIN relay lens in the depicted embodiment, and an output window 60 is used to seal the microscope.

Each of the above-described microscope configurations can be arranged to image a single object plane (single depth within the sample) at two different emission wavelengths, or two distinct object planes (different depths within the sample) at one or two emission wavelengths. As described above, two illumination sources can be coupled to the microscopes to provide stimulus for emission at two different wavelengths, or in some instances, two measured emission wavelengths can be stimulated by a single illumination wavelength. The characteristics of optical splitters 12A, 13A and 12B, 13B are selected based on the type of measurement being performed. For example, if the microscope of FIG. 1 or FIG. 4 is used to image object planes at different depths but the same wavelength, optical splitter 13A or 13B is an intensity division beam-splitter or polarization beam-splitter rather than a dichroic filter.

Figure 5:
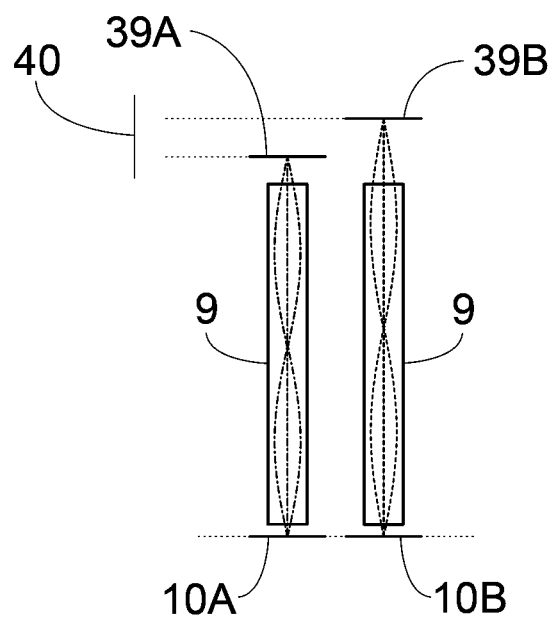
FIG. 5 is a pictorial diagram illustrating an optical path length shift in an exemplary miniaturized microscope system.

Referring now to FIG. 5, a two-color (two emission wavelength) single object plane configuration for the above-described microscopes is shown in a pictorial diagram. GRIN relay lens 9 is shown twice for clarity. First object plane 10A is imaged at a first image plane 39A and second object plane 10B, co-located with first object plane 10A is imaged at a different second image plane 39B. The optical path length between first object plane 10A and first image plane 39A differs from the optical path length between second object plane 10B and second image plane 39B, which is at least due to chromatic aberration within GRIN relay lens 9 as the emission wavelength received at first image plane 39A differs from the emission wavelength received at second image plane 39B. A resulting chromatic focal shift 40 corresponds to the difference in optical path length of the detection pathways (e.g., detection pathways 4A and 4B of FIG. 1) at their corresponding emission wavelengths, which are adjusted to co-locate object planes 10A and 10B at their corresponding emission wavelengths. The detection pathways of the microscope (e.g., detection pathways 4A and 4B of FIG. 1) are adjusted to co-locate object planes 5A and 5B of the microscope outside of objective lens 7A with a corresponding one of first image plane 39A and second image plane 39B, so that the two detection channels of the microscope ultimately image first object plane 10A and second object plane 10B at their corresponding emission wavelengths when, for example, cannula 2A is attached to microscope body 1A. In a configuration that does not employ GRIN relay lens 9, such as the microscope of FIG. 4, the detection pathways are adjusted to co-locate object planes 5A, 5B of the microscope at their corresponding emission wavelengths, which are set to some depth within the sample.

Figure 6:
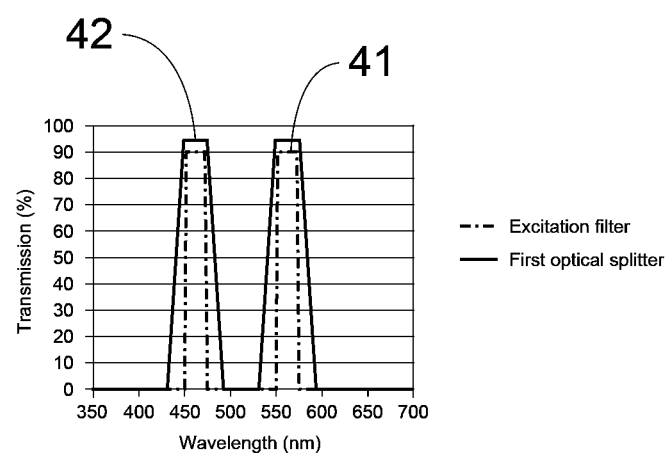
FIGS. 6-7 are graphs depicting optical transmission band characteristics of filters that may be used within the miniaturized multimodal microscope systems depicted herein.

Referring now to FIG. 6, characteristics of a first optical splitter (e.g., optical splitter 12A of FIG. 1) and an excitation filter (e.g., excitation filter 24A of FIG. 1) are shown for a two illumination color configuration. In the instant configuration, optical splitter 12A is a two pass-band dichroic filter for passing two illumination wavelengths and reflecting the emission wavelengths. Passbands 42 illustrate the passbands of optical splitter 12A. Excitation filter 24A may generally have a narrower passband characteristic 41 for purifying the spectra of the excitation illumination sources. In instances in which the two emission spectra are stimulated by a single illumination wavelength, a single passband will be present in each of optical splitter 12A and excitation filter 24A.

Referring now to FIG. 7, characteristics of a second optical splitter (e.g., optical splitter 13A of FIG. 1) and emission filters (e.g., emission filters 23A-23B of FIG. 1) are shown for a two emission color configuration. In the instant configuration, optical splitter 13A is a short-pass filter having a short-pass characteristic 43 for passing a first emission wavelength and reflecting a longer second emission wavelength, thereby separating the light returning from two imaged object planes 5A and 5B at two different corresponding wavelengths. Passbands 44A and 44B illustrate the passbands of emission filters 23A and 23B, respectively. For single emission wavelength applications, optical splitter 13A will generally be a wavelength-agnostic beam-splitter (intensity-division beam-splitter) or polarization beam-splitter that divides the light returning from the two object planes 5A and 5B equally and emission filters 23A and 23B will generally have an identical passband characteristic.

Figure 8:
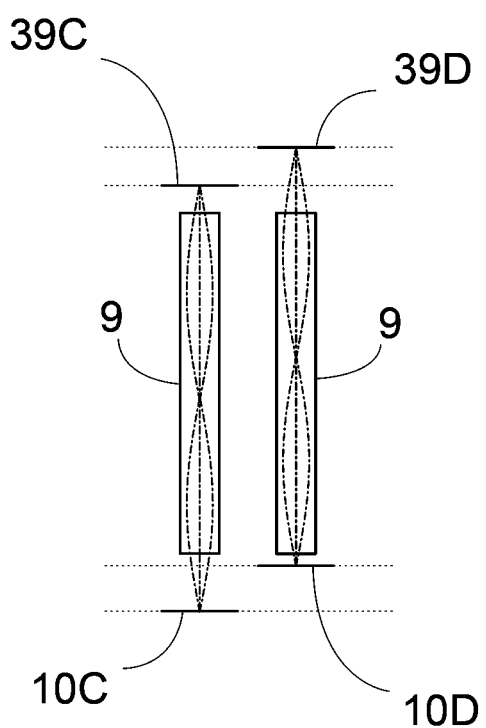
FIG. 8 is a pictorial diagram illustrating an optical path length and object plane shift in an exemplary miniaturized microscope system.
Figure 9:
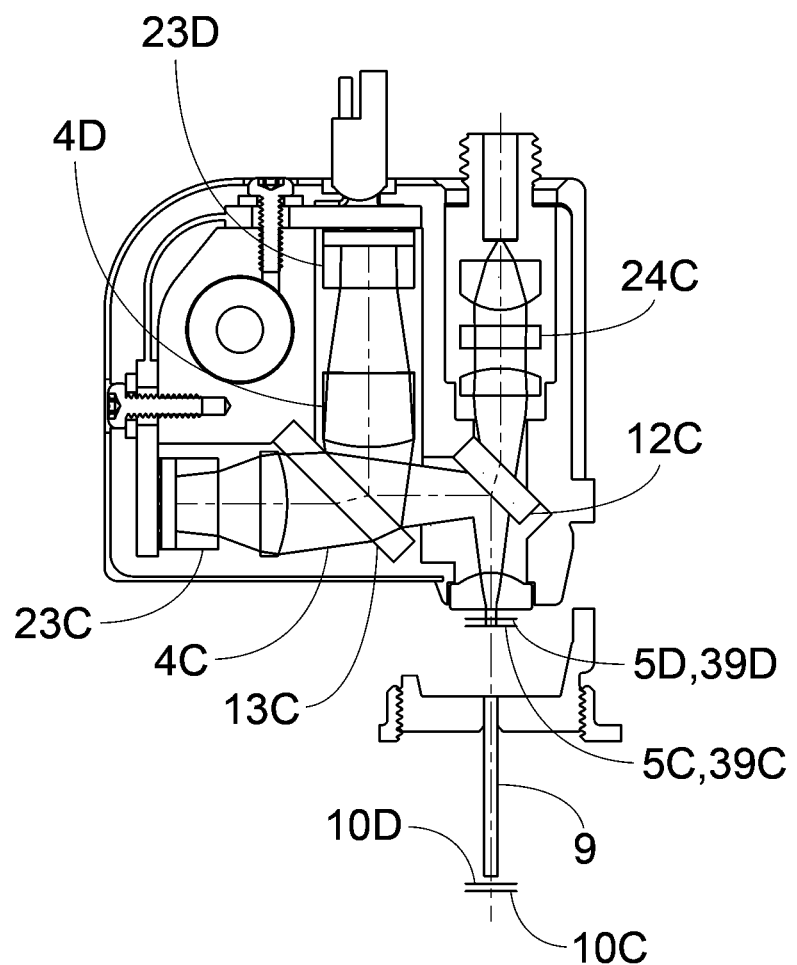
FIG. 9 is a side cross-section view of an exemplary miniaturized microscope system illustrating an object plane shift for single-wavelength measurement.

Referring now to FIG. 8, a single-color (single emission wavelength) dual object plane configuration for the above-described microscopes is shown in a pictorial diagram. GRIN relay lens 9 is again shown twice for clarity. A first object plane 10C is imaged at a first image plane 39C and a second object plane 10D, at a different depth within the sample from first object plane 10C is imaged at a different second image plane 39D. The optical path length between first object plane 10C and first image plane 39C does not differ from the optical path length between second object plane 10D and second image plane 39D, since the emission spectra is the same for both light received at first image plane 39C and light received at second image plane 39D. The optical path length of the detection pathways differ at the emission wavelength, in order to separate object planes 10C and 10D. Referring additionally to FIG. 9, a microscope having detection pathways 4C and 4D illustrates an arrangement that separates object planes 10C and 10D at a single emission wavelength by adjusting detection pathways 4C and 4D to locate object planes 5C and 5D at corresponding image planes 39C and 39D of FIG. 8. As described above for the instant configuration, an excitation filter 24C has a single-passband configuration, an optical splitter 13C is an intensity-division beam-splitter and emission filters 23C and 23D have identical single band-pass characteristics. An optical splitter 12C may have a short-pass characteristic that passes the excitation illumination wavelength and reflects the longer wavelength emitted light returning from the sample. In other configurations of the two-object plane system described above, an additional illumination wavelength may be provided for opto-genetic stimulation for stimulating light-driven ion channels in the sample. In such an application, excitation filter 24C has a dual band-pass characteristic to clean the illumination at the fluorescent excitation and opto-genetic stimulation wavelengths and optical splitter 12C also has a dual pass-band to pass both illumination wavelengths and to reflect the fluorescent emissions returning from the sample.

While the invention has been particularly shown and described with reference to the preferred embodiment thereof, it will be understood by those skilled in the art that the foregoing and other changes in form, and details may be made therein without departing from the spirit and scope of the invention.

What is claimed:

1. A miniature microscope for performing fluorescence measurements on a sample having an attached optical cannula, the microscope comprising:

a microscope body having at least one first connector for receiving at least one first optical illumination connection coupling light from at least one illumination source;

a second connector of the microscope body adapted to mechanically connect to the cannula and optically align the cannula with the microscope body and having a single optical interface for coupling light returning from the sample to the microscope and to couple light from the at least one illumination source to the sample;

a first optical splitter for separating the light returning from the sample coupled from the second connector from the light coupled from the illumination source to provide the light coupled from the illumination source to the second connector;

a second optical splitter for receiving the light returning from the sample from the first optical splitter and splitting the received light into a first image and a second image;

a first image sensor for receiving the first image from the second optical splitter; and a second image sensor for receiving the second image from the second optical splitter.

2. The microscope of claim 1, wherein the first optical splitter is a first optical filter disposed between the second optical splitter and the second connector, the first optical filter having a first dichroic characteristic that reflects the light returning from the sample and passes the illumination from the at least one illumination source.

3. The microscope of claim 2, wherein the second optical splitter is a second optical filter having a second dichroic characteristic for directing a portion of the light returning from the sample having a first wavelength corresponding to the first image to the first image sensor and directing a second portion of the light returning from the sample having a second wavelength corresponding to the second image to the second image sensor.

4. The microscope of claim 3, wherein the first dichroic characteristic of the first optical filter is a dual pass-band for directing light having two different wavelengths from two different illumination sources coupled to the at least one first connector to the sample and for reflecting the light returning from the sample along a first optical path to the first image sensor and along a second optical path to the second image sensor.

5. The microscope of claim 3, wherein the first dichroic characteristic of the first optical filter is a single pass-band for directing light from a single illumination source coupled to the at least one first connector to the sample, and wherein the second dichroic characteristic of the second optical filter is a short-pass characteristic for directing light reflected from the first optical filter having a first wavelength to the first image sensor and reflecting light reflected from the first optical filter having a second wavelength to the second image sensor.

6. The microscope of claim 3, further comprising an objective lens providing or coupled to the optical interface of the second connector.

7. The microscope of claim 6, wherein a first optical path extending from a first surface of the objective lens through which the light returning from the sample enters the objective lens to the first image sensor differs from a second optical path extending from the first surface of the objective lens to the second image sensor, and wherein the first and second optical paths are adjusted to image regions at a same object plane within the sample.

8. The microscope of claim 7, wherein the first image and the second image have the same magnification with respect to the object plane within the sample.

9. The microscope of claim 7, wherein a first optical path extending from a first surface of the objective lens through which the light returning from the sample enters the objective lens to the first image sensor differs from a second optical path extending from the first surface of the objective lens to the second image sensor, and wherein the first and second optical paths are adjusted to image regions at differing depths within the sample.

10. The microscope of claim 1, wherein the second optical splitter is an intensity division or polarization beam-splitter, and wherein a first optical path extending from a first object plane within the sample to the first image sensor differs from a second optical path extending from a second object plane within the sample to the second image sensor, whereby the first image sensor and the second image sensor image regions at differing depths within the sample.

11. The microscope of claim 1, wherein the second optical splitter is an optical filter having a second dichroic characteristic for directing light returning from the sample having a first wavelength to the first image sensor and reflecting light returning from the sample having a second wavelength to the second image sensor.

12. A method of performing simultaneous or sequential fluorescence measurements on a sample having an attached optical cannula, the method comprising:

first receiving an optical illumination connection coupling light from at least one illumination source at a first connector of a microscope;

mechanically connecting to the cannula with a second connector having at least one optical interface for coupling light returning from the sample to the microscope and illumination from the at least one illumination source to the sample;

second receiving the light returning from the sample at a first optical splitter integrated within the microscope;

first separating the light coupled from the at least one illumination source from the light returning from the sample with the first optical splitter;

second separating light returning from the sample coupled from the first optical splitter into a first image and a second image integrated within the microscope; and providing the separate first image and second image to corresponding ones of a pair of image sensors integrated within the microscope.

13. The method of claim 12, wherein the first optical splitter is a first optical filter disposed between the second optical splitter and the second connector, the first optical filter having a first dichroic characteristic that performs the first separating by reflecting the light returning from the sample and passes the illumination from the at least one illumination source.

14. The method of claim 12, wherein the second optical splitter is a second optical filter having a second dichroic characteristic that performs the second separating by directing a portion of the light returning from the sample having a first wavelength corresponding to the first image to the first image sensor and directing a second portion of the light returning from the sample having a second wavelength corresponding to the second image to the second image sensor.

15. The method of claim 14, wherein the first dichroic characteristic of the first optical filter is a dual pass-band for performing the first separating by directing light having two different wavelengths from two different illumination sources coupled to the at least one first connector to the sample and for reflecting the light returning from the sample along a first optical path to the first image sensor and along a second optical path to the second image sensor.

16. The method of claim 14, wherein the first dichroic characteristic of the first optical filter is a single pass-band for performing the first separating by directing light from a single illumination source coupled to the at least one first connector to the sample, and wherein the second dichroic characteristic of the second optical filter is a short-pass characteristic for performing the second separating by directing light reflected from the first optical filter having a first wavelength to the first image sensor and reflecting light reflected from the first optical filter having a second wavelength to the second image sensor.

17. The method of claim 14, further comprising collecting the light returning from the sample with an objective lens providing or coupled to the optical interface of the second connector.

18. The method of claim 17, wherein a first optical path extending from a first surface of the objective lens through which the light returning from the sample enters the objective lens to the first image sensor differs from a second optical path extending from the first surface of the objective lens to the second image sensor, and further comprising adjusting the first and the second optical paths to image regions at a same object plane within the sample.

19. The method of claim 18, wherein the first image and the second image have the same magnification with respect to the object plane within the sample.

20. The method of claim 18, wherein a first optical path extending from a first surface of the objective lens through which the light returning from the sample enters the objective lens to the first image sensor differs from a second optical path extending from the first surface of the objective lens to the second image sensor, and further comprising adjusting the first and the second optical paths to image regions at differing depths within the sample.

21. The method of claim 12, wherein the second separating separates the first image from the second image using an intensity division beam-splitter or polarization beam-splitter, and wherein a first optical path extending from a first object plane within the sample to the first image sensor differs from a second optical path extending from a second object plane within the sample to the second image sensor, whereby the first image sensor and the second image sensor image regions at differing depths within the sample.

22. The method of claim 12, wherein the second optical splitter is an optical filter having a second dichroic characteristic for performing the second separating by directing light returning from the sample having a first wavelength to the first image sensor and reflecting light returning from the sample having a second wavelength to the second image sensor.

23. A miniature microscope for performing fluorescence measurements on a sample having an attached optical cannula, the microscope comprising:

a microscope body having at least one first connector for receiving at least one first optical illumination connection coupling light from at least one illumination source;

a second connector of the microscope body adapted to mechanically connect to the cannula and optically align the cannula with the microscope body and having a single optical interface for coupling light returning from the sample to the microscope and to couple light from the at least one illumination source to the sample;

an objective lens provided at the second connector for collecting the light returning from the sample;

a first dichroic filter having a first dichroic characteristic for separating the light returning from the sample coupled from the second connector from the light coupled from the illumination source to provide the light coupled from the illumination source to the second connector;

a second dichroic filter for receiving the light returning from the sample from the first optical splitter and having a second dichroic characteristic for splitting the received light into a first image and a second image according to a corresponding first wavelength and second wavelength;

a first image sensor for receiving the first image from the second optical splitter; and a second image sensor for receiving the second image from the second optical splitter.

* * * * *